United States Patent [19]
Taylor et al.

[11] Patent Number: 5,254,687
[45] Date of Patent: Oct. 19, 1993

[54] PROCESS FOR THE PREPARATION OF PYRROLO[2,3-D]PYRIMIDINES

[75] Inventors: Edward C. Taylor; Hemantkumar H. Patel, both of Princeton, N.J.

[73] Assignee: The Trustees of Princeton University, Princeton, N.J.

[21] Appl. No.: 802,192

[22] Filed: Dec. 4, 1991

[51] Int. Cl.$^5$ .............................................. C07D 487/04
[52] U.S. Cl. ................................................... 544/280
[58] Field of Search ........................ 544/280; 514/258

[56] References Cited

U.S. PATENT DOCUMENTS 3,706,770 12/1972 Graf et al. ........................... 549/474
4,439,225 3/1984 Kollmeyer ........................... 549/474

Primary Examiner—Nicholas S. Rizzo
Attorney, Agent, or Firm—Mathews, Woodbridge & Collins

[57] ABSTRACT

5-Substituted pyrrolo[2,3-d]pyrimidines are prepared from a nucleophile of the formula $R^2-C(=NH)NH_2$ and a 2-amino-5-substituted-furan carrying a cyano or carboxy group in the 4-position. A typical example is the preparation of ethyl 4-(2-(2,4-diaminopyrrolo[2,3-d]pyrimidin-5-yl)ethyl}benzoate, an intermediate for the preparation of the known N-[4-{2-(2,4-diaminopyrrolo[2,3-d]pyrimidin-5-yl)ethyl}benzoyl]-L-glutamic acid, by allowing guanidine and ethyl 4-[2-(2-amino-3-cyanofur-4-yl)ethyl]benzoate to react under mild conditions.

5 Claims, No Drawings

PROCESS FOR THE PREPARATION OF PYRROLO[2,3-D]PYRIMIDINES

This invention pertains to a process for the preparation of compounds containing the pyrrolo[2,3-d]pyrimidine ring. This fused heterocyclic system can be depicted by the formula:

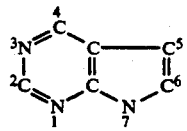

A variety of compounds containing this ring system have been described in the literature. 2-Amino-1,7-dihydropyrrolo[2,3-d]pyrimidin-4-one, also known as 7-deazapurine, for example, is reported by Davoll et al., J. Chem. Soc., 1960, 131. The pyrrolo[2,3-d]pyrimidine ring also is found in queuine, the aglycon of queuosine, and in the N-[4-{3-(2,4-diamino-7H-pyrrolo[2,3-d]pyrimidin-5-yl)-propyl}benzoyl]glutamic acid derivatives described in U.S. Pat. No. 4,997,838. 5-Aminoalkynylpyrrolo[2,3-d]pyrimidines are described in U.S. Pat. No. 5,047,519. Fluorescent dyes containing the pyrrolo[2,3-d]pyrimidine ring system are used as reagents to identify guanosine and adenosine terminators in the automated sequencing of DNA {See Cocuzza, Tetrahedron Lett., 29, No. 33, 4061}. EP-A 0432677 describes N-[4-(2-(2-hydroxy-4-amino-7H-pyrrolo[2,3-d]pyrimidin-5-yl)ethyl}benzoyl]glutamic acid and related compounds as being antineoplastic agents.

Typically in these compounds, the 2-position of the pyrrolo[2,3-d]pyrimidine ring will be unsubstituted or substituted with amino, but alternatively can carry an unsubstituted or substituted alkyl, aralkyl, aryl, alkylthio, aralkylthio, or arylthio group. The 4-position of the pyrrolo[2,3-d]pyrimidine ring generally will carry an oxo or amino group. (It will be appreciated that the 3-H-4-oxopyrrolo[2,3-d]pyrimidine structure is the tautomeric equivalent of the 4-hydroxypyrrolo[2,3-d]pyrimidine structure). The principal points of structural variation generally involves the 5- and 7-positions of the pyrrolo[2,3-d]pyrimidine structure, that is, the second carbon atom from the ring nitrogen atom and the ring nitrogen atom itself, respectively, of the pyrrole ring.

Substitution of the nitrogen atom in the 7-position generally does not pose a serious problems. Introducing a substituent in the 5-position, however, is considerably more problematical. One synthetic approach involves synthesizing the pyrrolo[2,3-d]pyrimidine system and then coupling this, typically as a 5-halo derivative, with a reagent carrying a precursor for the substituent in the 5-position. See e.g. Cocuzza, supra, and EP-A 0432677. This route requires synthesis of the 5-substituted pyrrolo[2,3-d]pyrimidine intermediates, which often is difficult, as well as the performance of a number of synthetic steps subsequent to coupling.

An alternative approach involves constructing the pyrrolo[2,3-d]pyrimidine ring through cyclization, as for example, allowing an α-dicyanomethyl derivative of a substituted alkanoic acid ester to react with guanidine. See e.g. U.S. Pat. No. 4,997,838.

The present process employs a new approach in which variation in what will become the 2-position of the pyrrolo[2,3-d]pyrimidine ring is incorporated into a nucleophilic reactant (the nature of which is hereinafter defined) while variation in the what will become the 4- and 5-positions of the pyrrolo[2,3-d]pyrimidine ring is incorporated into the substrate reactant (the nature of which also is hereinafter defined).

In particular, the process involves bringing a nucleophile of the formula:

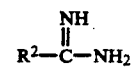

in which $R^2$ is hydrogen, amino, or an unsubstituted or substituted alkyl, aralkyl, aryl, alkylthio, aralkylthio, or arylthio group, into contact and under reactive conditions with a 2-aminofuran of the formula:

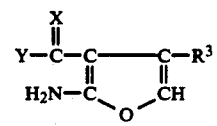

in which $R^3$ is a nucleophile-stable substituent and either (i) X is $=$ O and Y is an unsubstituted or substituted alkoxy, aralkoxy, aryloxy, alkylthio, aralkylthio, or arylthio group, or (ii) X and Y together are N≡. Thereby produced from this reaction is a pyrrolo[2,3-d]pyrimidine of the formula:

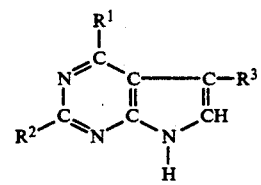

in which $R^2$ and $R^3$ are as defined above and $R^1$ is hydroxy or amino.

The reaction is straightforward, requiring no special equipment nor critical reaction conditions. The two reactants are simply heated in a solvent such as an alkanol and the solvent then removed as by simple evaporation. The product is isolated and the residue further purified by conventional methods such as recrystallization or chromatography.

Solely by reason of the groups predominantly found in the final compounds, $R^2$ in the first reactant generally will be hydrogen or amino. $R^2$ can, however, be a variety of other groups such as an unsubstituted or substituted alkyl, aralkyl, aryl, alkylthio, aralkylthio, or arylthio group. Typically the alkyl portion of these groups will contain 1 to 6 carbon atoms and the aryl groups will be an unsubstituted or substituted phenyl or naphthyl group.

When X and Y together are N≡, that is when a cyano group is present in a compound of Formula II, the pyrrolo[2,3-d]pyrimidine ring is formed with an amino group in the 4-position. Alternatively, when X is =O (so that X and Y are part of an ester or thioester), the pyrrolo[2,3-d]pyrimidine ring is formed with a hydroxy group in the 4-position. In this latter case, the nature of Y is relatively unimportant (since it does not appear in the final compounds). Typically Y will be an unsubstituted or substituted alkoxy, aralkoxy, aryloxy, alkylthio, aralkylthio, or arylthio group.

One advantageous feature of the process is the variation which is possible with respect to $R^3$ Thus with a 2-aminofuran appropriately substituted in the 3-position, a wide variety of distinct pyrrolo[2,3-d]pyrimidines are possible In practice, it is only necessary that $R^3$ be a nucleophile-stable substituent. Typical groups include phenylalkyl groups of 1 to 4 carbon atoms in the alkyl group including substituted phenyl, alkynyl groups including substituted alkynyl, formamido, halo, and the like.

One particularly valuable group of intermediates are those of the formula:

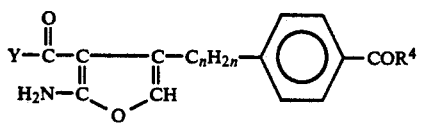

in which X and Y are as defined above, n has a value of 2 to 4, and $R^4$ is hydroxy or a carboxylic acid protecting group. By reacting such intermediates of Formula IV with a nucleophile of Formula I according to the present process, one can obtain intermediates of the formula:

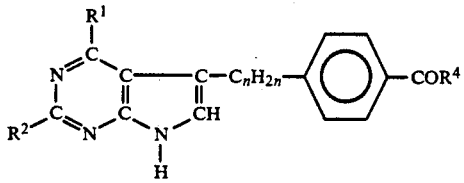

in which $R^1$, $R^2$, $R^4$, and n are as defined above.

Thus by allowing a compound of Formula V in which $R^4$ is hydroxy (that is, in which $COR^4$ is a carboxylic acid) or a reactive derivative thereof to react with a protected glutamic acid derivative under known amide forming conditions, a variety of previously described pharmaceutical agents (see EP-A 0432677 and U.S. Pat. No. 4,997,838) can be readily prepared.

Typical compounds of Formula IV include methyl 4-[2-(2-amino-3-cyanofur-4-yl)ethyl]benzoate, methyl 4-[3-(2-amino-3-cyanofur-4-yl)prop-1-yl]benzoate, ethyl 4-[2-(2-amino-3-cyanofur-4-yl)ethyl]benzoate, ethyl 4-[3-(2-amino-3-cyanofur-4-yl)prop-1-yl]benzoate, t-butyl 4-[2-(2-amino-3-cyanofur-4-yl)ethyl]benzoate, t-butyl 4-[3-(2-amino-3-cyanofur-4-yl)prop-1-yl]benzoate, methyl 4-[2-(2-amino-3-carbethoxyfur-4-yl)ethyl]benzoate, methyl 4-[3-(2-amino-3-carbethoxyfur-4-yl)prop-1-yl]benzoate, ethyl 4-[2-(2-amino-3-carbethoxyfur-4-yl)ethyl]benzoate, ethyl 4-[3-(2-amino-3-carbethoxyfur-4-yl)prop-1 -yl]benzoate, t-butyl 4-[2-(2-amino-3-carbethoxyfur-4-yl)ethyl]benzoate, t-butyl 4-[3-(2-amino-3-carbethoxyfur-4-yl)prop-1-yl]benzoate, methyl 4-[2-(2-amino-3-carbomethoxyfur-4-yl)ethyl]benzoate, methyl 4-[3-(2-amino-3-carbomethoxyfur-4-yl)prop-1-yl]benzoate, ethyl 4-[2-(2-amino-3-carbomethoxyfur-4-yl)ethyl]benzoate, ethyl 4-[3-(2 amino-3-carbomethoxyfur-4-yl)prop-1-yl]benzoate, t-butyl 4-[2-(2-amino-3-carbomethoxyfur-4-yl)ethyl]benzoate, t-butyl 4-[3-(2-amino-3-carbomethoxyfur-4-yl)prop-1-yl]benzoate, and the like.

A second but related class of intermediates are those of the formula:

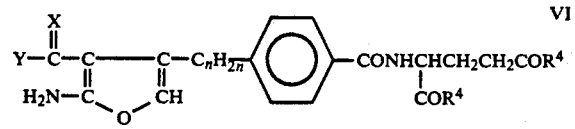

in which X and Y are as defined above, n has a value of 2 to 4, and $R^4$ is a carboxylic acid protecting group. By reacting intermediates of Formula VI with a nucleophile of Formula I according to this process, one can obtain the immediate precursors for the pharmaceutical agents of EP-A and U.S. Pat. No. 4,997,838, requiring only the removal of the carboxylic acid protecting groups depicted by $R^4$.

The 2-aminofuran intermediates of Formula II are readily prepared by allowing an α-hydroxyketone of Formula II to react with malononitrile or an alkyl cyanoacetate of Formula VIII:

in which X and Y are as defined above. This reaction again is straightforward, the two reactants simply being stirred in a solvent such as an alkanol in the presence of triethylamine.

Malononitrile and a wide variety of alkyl cyanoacetate of Formula VIII are known. The c-hydroxyketones of Formula VII can be readily prepared from the corresponding aldehydes of Formula IX by use of formaldehyde in the presence of a catalytic amount of ethyl benzothiazolium bromide and triethylamine:

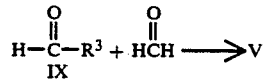

Since all these reactions proceed under extremely mild conditions, the only structural restraint placed on $R^3$ in the 2-aminofuran intermediates of Formula II is that it should be relatively stable in the presence of the nucleophile of Formula I in forming the pyrrolo[2,3-d]pyrimidine ring system.

The following examples will serve to further typify the nature of the present invention.

EXAMPLE 1

Ethyl 4-(4-Hydroxy-3-oxobutyl)benzoate

A mixture of 1.1 g (5 mmol) of 3-(4-carbethoxyphenyl)propanal and 150 mg (5 mmol) of paraformaldehyde in 10 mL of ethanol, together with 230 mg (0.9 mmol) of ethyl benzothiazolium bromide and 90 mg (0.9 mmol) of triethylamine, is heated at about 70° C. for 16 hours. The reaction mixture is concentrated in vacuo and the product further purified by chromatography on silica gel, eluting with 15:85 ethyl acetate:hexane, to yield ethyl 4-(4-hydroxy-3-oxobutyl)benzoate as a colorless oil which solidifies upon standing; m.p. 51°–52° C. Anal. calcd for $C_{13}H_{16}O_4$: C, 66.09; H 6.83. Found: C, 66.29; H, 6.70.

EXAMPLE 2

Ethyl 4-[2-(2-Amino-3-cyanofur-4-yl)ethyl]benzoate

A mixture of 2.36 g (10 mmol) of ethyl 4-(4-hydroxy-3-oxobutyl)benzoate, 0.66 g. (10 mmol) of malononitrile, and 1.01 g (10 mmol) of triethylamine in 10 mL of ethanol is stirred at 25° C. for 10 hours. Ethyl 4-[2-(2-amino-3-cyanofur-4-yl)ethyl]benzoate is formed as a solid and can be collected by filtration. After washing with a small amount of methylene chloride and drying, a white solid is obtained; m.p. 195°–197° C. Anal. calcd for $C_{16}H_{16}N_2O_3$: C, 67.60; H, 5.67; N, 9.85 Found: C, 67.85; H, 5.71; N, 10.14.

EXAMPLE 3

Ethyl 4-{2-(2,4-Diaminopyrrolo[2,3-pyrimidin-5-yl)-ethyl)-benzoate

To a solution of guanidine free base (prepared from 105 mg of guanidine hydrochloride and 60 mg of sodium ethoxide) in 10 mL of anhydrous ethanol are added 284 mg (1 mmol) of ethyl 4-[2-(2-amino-3-cyanofur-4-yl)ethyl]benzoate. The mixture is heated at reflux for 30 hrs and the solvent then evaporated in vacuo. The residue is chromatographed on silica gel, eluting with 5:95 methanol:methylene chloride, to yield ethyl 4-{2-(2,4-diaminopyrrolo[2,3-d]pyrimidin-5-yl)ethyl}benzoate as a light brown solid; m.p. 202°–204° C. Mass spectrograph calculated for $C_{17}H_{19}N_5O_2$: 325.1538, Found: 325.1543.

EXAMPLE 4

N-[4-(2-(2,4-Diaminopyrrolo[2,3-d]pyrimidin-5-yl)-ethyl}benzoyl]-L-glutamic Acid By subjecting the ethyl 4-{2-(2,4-diaminopyrrolo[2,3-d]pyrimidin-5-yl)ethyl}benzoate obtained in Example 3 to the known steps of saponification, coupling with diethyl L-glutamate, and removal of the glutamic acid protecting groups as through saponification in the manner described in U.S. Pat. No. 4,997,838, there is obtained N-[4-{2-(2,4-diaminopyrrolo[2,3-d]pyrimidin-5-yl)ethyl}benzoyl]-L-glutamic acid, m.p. 258°–262° C.

EXAMPLE 5

N-[4-{3-(2,4-Diaminopyrrolo[2,3-d]pyrimidin-5-yl)prop-1-yl}-benzoyl]-1-glutamic Acid By substituting the known 4-(4-carbethoxyphenyl)-butanal (see U.S. Pat. No. 4,895,946) in the procedure of Example 1, there is obtained ethyl 4-(5-hydroxy-4-oxopentyl)benzoate. By subjecting this the procedure of Examples 2, there is obtained ethyl 4-[3-(2-amino-3-cyanofur-4-yl)prop-1-yl]benzoate. This in turn is allowed to react with guanidine free base in the identical manner to that described in Example 3 to yield ethyl 4-{3-(2,4-diaminopyrrolo[ 2,3-d]pyrimidin-5-yl)prop-1-yl}benzoate which, in an identical fashion to that set forth in Example 4, is saponified to yield 4-{3-(2,4-diaminopyrrolo[2,3-d]pyrimidin-5-yl)prop-1-yl}benzoic acid which in turn is coupled with diethyl L-glutamate to yield diethyl N-[4-{3-(2,4-diaminopyrrolo[2,3-d]pyrimidin-5-yl}prop-1-yl}benzoyl]-L-glutamate which in turn is saponified with sodium hydroxide to yield N-[4-{3-(2,4-diaminopyrrolo[2,3-d]-pyrimidin-5-yl)prop-1-yl}benzoyl]-L-glutamic acid, m.p. >250° C.

EXAMPLE 6

N-[4-(2-(2-Amino-4-hydroxypyrrolo[2,3-d]pyrimidin-5-yl)-ethyl}benzoyl]-L-glutamic Acid By substituting an equivalent amount of ethyl cyanoacetate for malononitrile in Example 2, there is obtained ethyl 4-[2-(2-amino-3-carbethoxyfur-4-yl)ethyl]-benzoate. This is allowed to react with guanidine free base in the identical manner to that described in Example 3 to yield ethyl 4-[2-(2-amino-4-hydroxypyrrolo[2,3-d]pyrimidin-5-yl)ethyl]benzoate which in a similar fashion is hydrolysed to yield 4-[2-(2-amino-4-hydroxypyrrolo[2,3-d]pyrimidin-5-yl)ethyl]benzoic acid which in turn is coupled with diethyl L-glutamate. Saponification of the resulting diethyl N-[4-{2-(2-amino-4-hydroxypyrrolo[2,3-d]pyrimidin-5-yl)ethyl}-benzoyl]-L-glutamate in the manner described in U.S. Pat. No. 4,997,838 then yields N-[4-{2-(2-amino-4-hydroxypyrrolo-[2,3-d]pyrimidin-5-yl)ethyl}benzoyl]-L-glutamic acid, m.p. 257°–258° C. (dec.).

EXAMPLE 7

N-[4-(3-(2-Amino-4-hydroxypyrrolo[2.3-d]pyrimidin-5-yl)prop-1-yl}benzoyl]-L-glutamic Acid By substituting 4-(4-carbethoxyphenyl)butanal for 3-(4-carbethoxyphenyl)propanal in the procedure of Example 1 and thereafter substituting an equivalent amount of ethyl cyanoacetate for malononitrile in Example 2, there is obtained ethyl 4-[3-(2-amino-3-carbethoxyfur-4-yl)prop-1-yl]benzoate which thereafter is treated with guanidine in free base as described above to yield ethyl 4-[3-(2-amino-4-hydroxypyrrolo[2,3-d]-pyrimidin-5-yl)prop-1-yl]benzoate. This is subjected to saponification to yield 4-[3-(2-amino-4-hydroxypyrrolo[2,3-d]pyrimidin-5-yl)prop-1-yl]benzoic acid which then is coupled with diethyl L-glutamate, and the resulting diethyl N-[4-{3-(2-amino-4-hydroxypyrrolo[2,3-d]-pyrimidin-5-yl)prop-1-yl}benzoyl]-L-glutamate is saponified to yield N-[4-(3-(2-amino-4-hydroxypyrrolo[2,3-d]pyrimidin-5-yl)prop-1-yl}benzoyl]-L-glutamic acid, m.p. 190°–193° C.

What is claimed is:

1. Process for the preparation of pyrrolopyrimidines which comprises bringing a nucleophile of the formula:

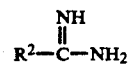

in which $R^2$ is hydrogen, amino, or an unsubstituted or substituted alkyl, aralkyl, aryl, alkylthio, aralkylthio, or arylthio group, into contact with a 2-aminofuran of the formula:

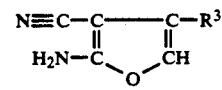

in which $R^3$ is a nucleophile-stable substituent, under reactive conditions to produce a pyrrolopyrimidine of the formula:

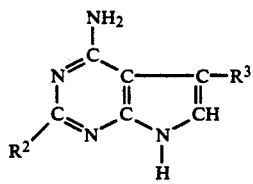
in which R² and R³ are as defined above.
2. The process according to claim 1 wherein R² is hydrogen or amino.
3. The process according to claim 1 wherein said 2-aminofuran has the formula:
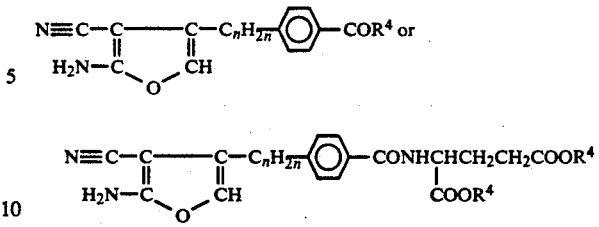
wherein n has a value of 2 to 4; and
R⁴ is a carboxylic acid protecting group.
4. The process according to claim 3 in which n has a value of 2.
5. The process according to claim 3 in which n has a value of 3.
* * * * *